(12) United States Patent
Mitchel et al.

(10) Patent No.: US 9,830,574 B2
(45) Date of Patent: *Nov. 28, 2017

(54) SYSTEM AND METHOD FOR COLLECTING, PROCESSING, AND STORING DISCRETE DATA RECORDS BASED UPON A SINGLE DATA INPUT

(71) Applicants: Jules T. Mitchel, New York, NY (US); Joyce B. Hays, New York, NY (US)

(72) Inventors: Jules T. Mitchel, New York, NY (US); Joyce B. Hays, New York, NY (US)

(*) Notice: Subject to any disclaimer, the term of this patent is extended or adjusted under 35 U.S.C. 154(b) by 684 days.

This patent is subject to a terminal disclaimer.

(21) Appl. No.: 13/786,683

(22) Filed: Mar. 6, 2013

(65) Prior Publication Data
US 2013/0185098 A1  Jul. 18, 2013

Related U.S. Application Data

(60) Continuation-in-part of application No. 13/234,623, filed on Sep. 16, 2011, which is a division of application No. 12/505,206, filed on Jul. 17, 2009, now Pat. No. 8,041,581.

(60) Provisional application No. 61/081,938, filed on Jul. 18, 2008.

(51) Int. Cl.
| G06Q 50/00 | (2012.01) |
| G06Q 10/10 | (2012.01) |
| G06Q 50/24 | (2012.01) |
| G06F 17/30 | (2006.01) |
| G06F 19/00 | (2011.01) |
| G06Q 50/22 | (2012.01) |

(52) U.S. Cl.
CPC ....... *G06Q 10/10* (2013.01); *G06F 17/30011* (2013.01); *G06F 19/322* (2013.01); *G06F 19/363* (2013.01); *G06Q 50/22* (2013.01); *G06Q 50/24* (2013.01)

(58) Field of Classification Search
CPC .......................................... G06Q 50/22–50/24
See application file for complete search history.

(56) References Cited

U.S. PATENT DOCUMENTS

| 4,958,276 A * | 9/1990 | Kiuchi | G06F 9/3802 |
| | | | 711/167 |
| 6,854,086 B2 * | 2/2005 | Umen et al. | 715/236 |
| 6,925,599 B2 * | 8/2005 | Wood | 715/229 |
| 7,669,114 B2 * | 2/2010 | Wood | 715/205 |
| 7,752,057 B2 * | 7/2010 | Ikeguchi et al. | 705/2 |

(Continued)

OTHER PUBLICATIONS

Amor, Rudy. "PACS Overview: Past, Present, and Future", Biomedical Instrumentation & Technology; Jul./Aug. 2006; vol. 40, No. 4, p. 281-2.*

*Primary Examiner* — Robert Sorey
(74) *Attorney, Agent, or Firm* — Kohn & Associates PLLC

(57) ABSTRACT

A system and method for the collection, capture, processing, storage, and tracking of data for both electronic clinical trial and electronic heath records based upon a single data collection instance, and including data collected by electronic medical devices. Devices and methods for creating certified digital image copies of original documents, including paper source documents for a clinical trial. Devices and methods for ensuring the secure archiving of original electronic documents, including electronic clinical trial source documents, in a secure document storage server.

2 Claims, 4 Drawing Sheets

(56) References Cited

U.S. PATENT DOCUMENTS

| | | | |
|---|---|---|---|
| 2002/0111946 A1* | 8/2002 | Fallon | 707/9 |
| 2003/0187688 A1* | 10/2003 | Fey et al. | 705/2 |
| 2003/0208378 A1* | 11/2003 | Thangaraj et al. | 705/2 |
| 2004/0078216 A1* | 4/2004 | Toto | 705/2 |
| 2004/0093240 A1* | 5/2004 | Shah | G06F 19/363 705/2 |
| 2004/0243439 A1* | 12/2004 | Huggard et al. | 705/2 |
| 2005/0010451 A1* | 1/2005 | Marks et al. | 705/3 |
| 2005/0038673 A1* | 2/2005 | Stookey et al. | 705/2 |
| 2005/0055241 A1* | 3/2005 | Horstmann | 705/2 |
| 2005/0075832 A1* | 4/2005 | Ikeguchi et al. | 702/179 |
| 2005/0210026 A1* | 9/2005 | Wood | 707/5 |
| 2006/0248373 A1* | 11/2006 | Warman et al. | 714/4 |
| 2006/0259783 A1* | 11/2006 | Work et al. | 713/189 |
| 2007/0005393 A1* | 1/2007 | Cole et al. | 705/2 |
| 2008/0040151 A1* | 2/2008 | Moore | G06F 19/322 705/2 |
| 2008/0059241 A1* | 3/2008 | Zahlmann et al. | 705/3 |
| 2008/0086337 A1* | 4/2008 | Soon-Shiong | 705/3 |
| 2008/0154640 A1* | 6/2008 | DeMeyer et al. | 705/2 |
| 2008/0183497 A1* | 7/2008 | Soon-Shiong | 705/2 |
| 2008/0256128 A1* | 10/2008 | Pierce et al. | 707/104.1 |
| 2008/0270420 A1* | 10/2008 | Rosenberg | 707/10 |
| 2011/0161101 A1* | 6/2011 | Ikeguchi et al. | 705/2 |

* cited by examiner

SYSTEM AND METHOD FOR COLLECTING, PROCESSING, AND STORING DISCRETE DATA RECORDS BASED UPON A SINGLE DATA INPUT

FIELD OF THE INVENTION

The present invention generally relates to the field of electronic data collection and the processing. Specifically the invention relates to the areas of collecting a single set of data, capturing the data as an electronic source document, processing the data into a variety of formats, and storing the various processed data records in discrete databases.

DESCRIPTION OF RELATED ART

Clinical trials require the collection and storage of medical records, the coordination of records among several research entities, and the exposure of records to inspection by sponsoring entities and regulatory agencies. These tasks are greatly facilitated by the electronic record collection, processing, and storage. Electronic records management permits more efficient entry of data into subject records, facilitates the extraction and analysis of data from records, and allows the rapid assembly of records for auditing. The United States Food and Drug Administration (FDA) and other regulatory agencies accept the use of electronic record management systems in clinical trials. Title 21 CFR 11 has been promulgated to define criteria under which electronic records and electronic signatures are considered to be trustworthy, reliable, and equivalent to paper records.

The requirements for the creation and handling of source documents and clinical trial records according to 21 CFR 11 are interpreted in guides published or adopted by the FDA, including *Guidance for Industry E6 Good Clinical Practice: Consolidated Guidance* (1996) ("ICH E6"), and *Electronic Source Documentation in Clinical Investigations* (2010) ("E-Source"). A source document is defined as "(o)riginal documents, data and records (e.g., hospital records, clinical and office charts, laboratory notes, memoranda, subjects' diaries of evaluation checklists, pharmacy dispensing records, recorded data from automated instruments, copies or transcriptions certified after verification as being accurate and complete, microfiches, photographic negatives, microfilm or magnetic media, x-rays, subject files, and records kept at the pharmacy, at the laboratories, and at medico-technical departments involved in the clinical trial)" ICH E6Sec. 1.52. A case report form (CRF) is a document defined as "(a) printed, optical, or electronic document designed to record all of the . . . information . . . on each trial subject" ICH E6 Sec. 11.2. Data reported in a CRF can be derived from source documents. A CRF can itself be a source document, if clinical trial observations are entered directly into the CRF. A copy of a source document is itself considered to be a source document if it is certified to be an exact copy having all of the same attributes and information as the original ICH E6 Sec. 1.52 and E-Source Glossary.

An electronic records system must allow auditors to compare data in a CRF to be compared with data in the source documents, so that discrepancies can be detected, explained and corrected as needed, and the accuracy of the data in the CRF is confirmed. ICH E6 Sec. 4.9.2.

Electronic source documents and CRFs include data elements.Each element represents an individual observation by an authorized data originator. Each data element includes data attributes. Data attributes include the data themselves, such as a blood pressure or a temperature reading, and data element identifiers, such as the identity of the originator, the date of entry, and the study subject to which the data element belongs. When new data elements are added to an existing electronic CRF (eCRF), each new data element must be permanently linked to the electronic signature and/or digital certificate of its originator. This indicates the signing party's identity and approval of the document, and provides evidence of the document's integrity. Data elements in an eCRF can be corrected if found to be erroneous, but the original data element must remain present in the eCRF, and the correction must be accompanied by data element identifiers explaining the reason for the correction and the digital signature of the party making the correction. E-Source Sec. III.A. Taken together, the data element identifiers incorporated into an electronic source document create an audit trail, a computer generated, time stamped electronic record that allows reconstruction of the data-related events occurring during the creation and modification deletion of an electronic record as required by 21 CFR 11.10(e). An audit trail allows each data element to be traced to its ultimate originator, and to prevent an originator from denying legal responsibility for the element.

21 CFR §11 also mandates that a clinical trial records management system be capable of generating accurate and complete copies of records in both human readable and electronic form suitable for inspection, and protecting of records for accurate and ready retrieval throughout the records retention period. 21 CFR §11.10.

Currently, electronic data entry and storage of patient information in clinical trials is rare except for some dedicated Phase 1 units. This is due to the fact that current electronic record management systems, particularly those that are web-based, often fail to comply with the regulations pertaining to the capture and management of electronic source documents as related to clinical trial data.

One shortcoming of existing electronic record management systems is the lack of capacity to create certified copies of paper source documents in electronic form. After completion of a clinical trial, paper source documents must be collected and audited by the FDA or other regulatory agency before the clinical trial is approved. The organization, collection, and transmission of paper source documents from multiple trial sites is time consuming, expensive, and error-prone, and can greatly delay regulatory approval. The secure storage and inventory of paper source documents also consume time and resources. The conversion of original paper source documents to certified electronic copies would eliminate the need for handling and storing, paper source documents, since a certified copy of a source document is itself considered to be a source document. ICH E6 Sec. 1.52. At present, however, no means exists to certify an electronic copy of a paper source document by permanent attachment of a certification that the copy is an exact copy having all of the same attributes and information as the original. There is a need for an electronic records management system and method that enables an authorized user to compare a paper original source document to an electronic copy and permanently affix a permanent digital certification to the electronic copy.

Another shortcoming of existing electronic record management systems is in the archiving of electronic records for the inspection of regulatory agencies. After completion of a clinical trial, the FDA, for example, must complete a records audit before it will grant approval of a drug or medical device. Reliable original source documents must be readily available for comparison to the records used to compile data in a clinical trial, so that discrepancies can be detected, explained, and corrected. Existing electronic record management systems do not guarantee that electronic source documents and eCRFs are available to auditors in exactly the form in which they were first captured. In existing medical record management systems, electronic records are typically stored in a clinical trial database under the control of the parties conducting the clinical trial, and accessible to authorized participants in the clinical trial. In the environment of a clinical trial database, electronic records are subject to accidental or deliberate alteration. They cannot be assumed to be preserved in their original form and so do not meet the requirements of 21 CFR §11.10. There is a need for a system and methods that ensure the archiving of original electronic source documents before they are exposed to a clinical trial database accessible to trial participants and other parties interested in the outcome of the clinical trial.

Electronic clinical trial data can be produced by electronic medical instruments. Electronic instruments such as sphygmomanometers and blood chemistry analyzers can record clinical data directly from subjects of clinical trials, but the data must still be transcribed or otherwise transformed for entry into clinical trial source documents. There is a need for an electronic medical records management system capable of capturing data from electronic medical devices directly in the form of electronic source documents that meet the standards set by 21 CFR 11.

SUMMARY OF THE INVENTION

The present invention provides an electronic records management system for the collection, capture, processing, storage and tracking of data for both electronic source health records and for clinical trial purposes, including a certification module for creating a certified digital image copy of an original paper source document. The present invention also provides a method for creating a certified digital image copy of a paper source document including the steps of uploading a modifiable digitized image of a paper source document into a document memory, displaying the modifiable digital image copy on a certification interface, comparing the modifiable digital image copy to the paper source document, determining that the modifiable image copy is an exact copy of the paper source document, certifying the modifiable digital image copy to be an exact copy of the paper source document by permanent attachment of an electronic signature to the modifiable digital image copy by means of a copy processor, and rendering the certified digital image copy unmodifiable by means of the copy processor. The present invention also provides an electronic records management system including medical devices for collecting clinical data in electronic form, and a central data server for capturing the clinical data in the form of an electronic source document. The present invention further provides an electronic records management system including a gating device and gating method for ensuring that an electronic clinical trial source document at a central data server is archived in a server under the control of a disinterested party before it is released to a clinical trial database. The present invention also provides a device and a method for creating a digital image copy of an original document and certifying the digital image to be an exact copy of the original document. The present invention further provides a device and a method for ensuring the archiving of an electronic file in an archiving device before the electronic file is transmitted from a first storage device to a second storage device,

DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION OF THE INVENTION

Figure 1:
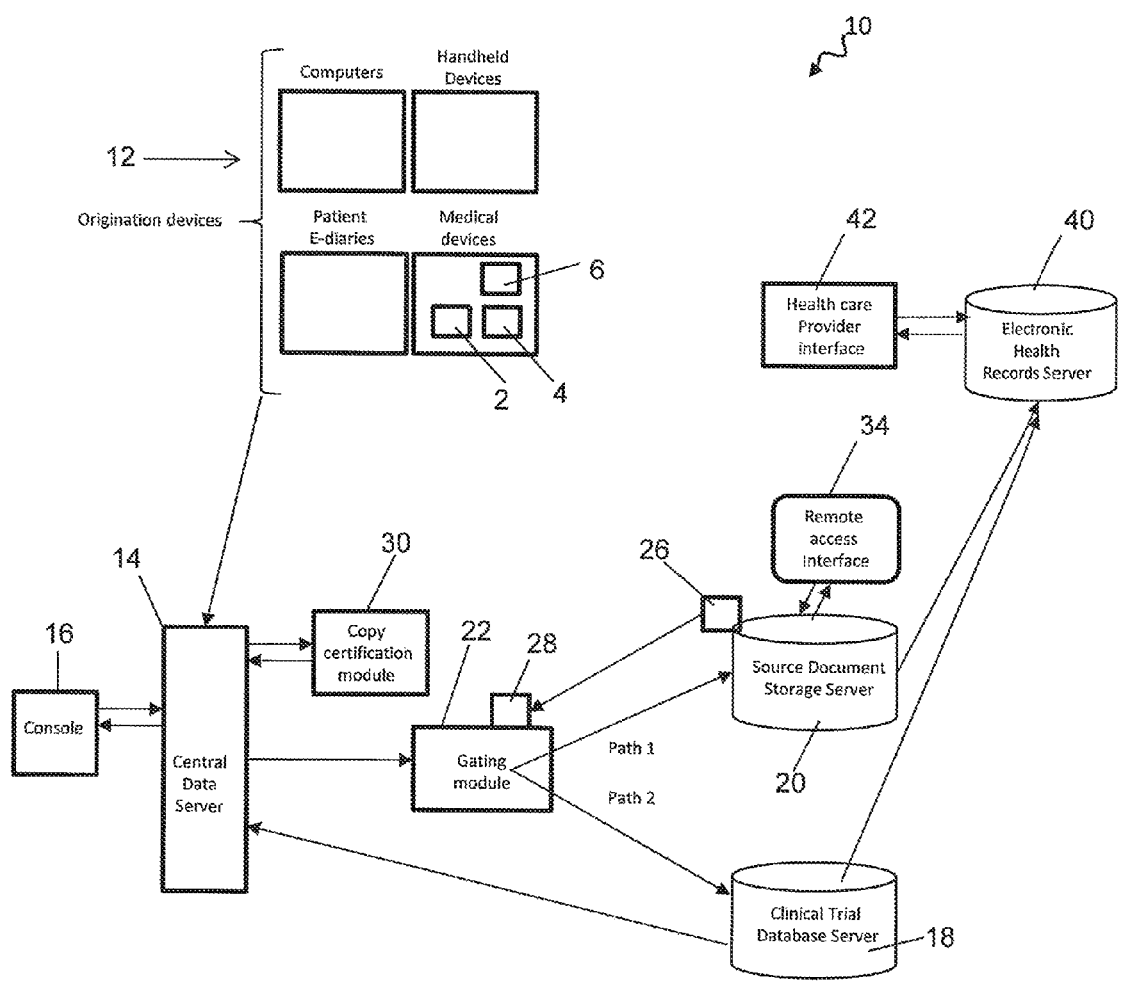
FIG. 1 represents a conceptual overview diagram of the architecture of the electronic records management system of the present invention, with solid arrowheads indicating the flow of information among components of the system.

An electronic records management system according to the present invention is generally indicated at 10. FIG. 1 represents a diagram of the system's basic architecture and functionality. The electronic records management system includes at least one data origination device 12 for the collection of clinical trial data by a data originator at one or more clinical trial sites or from authorized off-site locations. In the context of the present invention, and consistent with FDA guidelines, a data originator is defined as a person or automated medical device authorized to enter data into source documents. The data origination devices include, but are not limited to, computers of the desktop, work station, laptop, and tablet types; smartphones, digital assistants, and other hand-held devices, including any device for recording a patient's diary.

Data origination devices according to the present invention also include medical devices that collect, store, and/or transmit biological data from a subject in electronic form. These devices include any user operated or autonomous device that monitors and/or analyzes subject parameters such as bodily fluids, signals, and functions, and electronically stores or transmits the resulting data. For the purposes of the present invention, medical devices include, but are not limited to, thermometers, sphygmomanometers, glucose monitors, blood chemistry and gas analyzers, electrocardiographs, infusion pumps, and ventilators. Preferably, the medical devices include at least a processor 2 for collecting, analyzing and digitizing data, a communications interface 4 to communicate with a central data server 14, and memory 6 sufficient to store data until transmission to the central data server 14. Users such as data originators and investigators preferably interact with the medical records system 10 by means of a user interface (not shown) deployed via a series of web pages, but the system 10 can function using a proprietary software program as well.

Data collected by the data origination devices 12 are transmitted to the central data server 14, which captures clinical trial data as an electronic source document. Preferably the data are transmitted via the Internet, but the data can alternatively be relayed by any suitable networking protocol via wired or wireless local, metropolitan, and wide area networks. The operation of the central data server 14 is preferably supervised by an administrator-operated console 16. The central data server is also accessible to authorized users through at least one user interface (not shown). The central data server 14 is not necessarily a single physical entity, but can be a virtual server including a plurality of servers distributed at various local and distant sites, the servers being networked together to function as a central data server 14.

In addition to its data capture functionality, the central data server 14 provides at least temporary record storage and runs software to control the formatting, copying, and flow of records through the records management system. Administrators of the records management system 10 can, by means of the console 16, regulate and track the issuance and storage of passwords, the assignment of permitted roles in record management to users, and the authentication of users logging onto the system 10. For example, a data originator can be permitted to enter data into a source document, and an investigator can be permitted both to enter data and review and approve an eCRF, in accordance with FDA guidelines for roles in a clinical trial. The console 16 preferably includes the console disclosed in U.S. Patent Application Publication US2007/0124346 to Mitchell et al., which is herein incorporated in its entirety.

The central data server 14 preferably captures incoming data as a human-readable electronic source document, in formats including but not limited to PDF, XML, JPEG, or the data table files of any suitable database known in the art. In addition, in the preferred embodiment, central data server 14 populates existing source documents such as eCRFs with new and/or modified data elements submitted by authorized originators and investigators. The captured data elements include data element identifiers such as the identity of the originator, the date of addition or modification, and the reason for the addition or modification. If the originator is a device or instrument, the central data server 14 captures a data element identifier that identifies the instrument and the authority that validated it for use. Preferably, the central data server 14 also assigns and links identifying document attributes to the electronic source document, such as a serial number and a characteristic such as "new source document" or "modified eCRF". All of the data element identifiers linked to an electronic source document constitute an audit trail of data-related events for that document. In the preferred embodiment, these data-related events are collected and recorded in a log maintained preferably in the central data server 14

In the preferred embodiment, the electronic records management system 10 also includes a clinical trial data base server 18, which stores electronic records for access by authorized participants in the clinical trial; a source document storage server 20, to archive electronic source documents for access by auditors and regulators of a clinical trial but not by participants in the clinical trial; and a gating module 22 interconnecting the central data server 14 to both the source document storage server 20 and the clinical trial database server 18. The source document storage server 20 and clinical trial database server 18 need not be individual physical entities but can be a virtual servers, each including a plurality of networked servers distributed at various local and distant sites.

In the preferred embodiment, the source document storage server 20 is not under the control of the participants in a clinical trial, such as data originators, investigators, and other parties having an interest in outcome of the clinical trial. Preferably, the source document storage server 20 is maintained and controlled by a third party independent of the clinical trial, and more preferably a third party disinterested in the outcome of the clinical trial. The source data server 20 serves as an independent repository of archived electronic source documents. These documents can be accessed through at least one remote access interface 24 by regulatory agencies and any other parties authorized to monitor the quality and integrity of the electronic source documents. Previously, these parties could only ensure this degree of data integrity by reviewing the collected paper source documents.

In contrast, source documents and other electronic records stored in the clinical trial database server 18 are accessible to authorized participants in a clinical trial. Preferably they are stored in an unlocked form, so that authorized participants can extract data for the preparation of summaries, analyses, and reports. The copying, transfer, and processing of data in the clinical trial database server 18 introduces the possibility of data alteration and corruption, both intentional and unintentional.

The gating module 22 performs an enforced archiving function, allowing an electronic source document to be transmitted to the clinical trial database server 18 only after that electronic source document has first been archived in the source document storage server 20. This enforced archiving function ensures that a pristine, original version of an electronic source document is archived securely and out of the control of the parties running the clinical trial. This greatly increases the efficiency and speed of regulatory audits. Regulators and other auditing parties can compare the archived source document to the version on the clinical trial database server, and to reports derived from that version, with confidence that the archived source document truly represents the data as observed by its originator.

The gating module 22 performs its enforced archiving function by controlling a branch point interconnecting the central data server 14 to the source document storage server 20 via a first path, and interconnecting the central data server 14 to the clinical trial database server 18 via a second path, as best shown in FIG. 1.

The gating module 22 is settable to allow transmission of electronic documents either along the first path or the second path. In its default setting, the gating module 22 opens the first path to allow transmission of a source document from the central data server 14 to the source document storage server 20 for secure archiving. The source document storage server 20 includes an acknowledgment signal generator 26 to transmit an acknowledgment signal after an electronic document has been successfully archived. The gating module 22 includes an acknowledgment signal receiver 28 to receive the acknowledgment signal. Preferably, the acknowledgement signal is transmitted via the same network and transmission protocol utilized to transmit documents among the components of the system 10, but the signal can alternatively be transmitted by any means known in the art, including but not limited to Bluetooth, WiFi, and mobile phone protocols.

Upon receipt of an acknowledgment signal, the gating module 22 resets to open the second path to allow the electronic document to be transmitted from the central data server 14 to the clinical trial database server 18. Preferably, the gating module 22 is also configured to close the first path upon receipt of an acknowledgment signal, so that the first and second paths are never simultaneously open. This is a further safeguard of the integrity of the secure document storage server 20.

Figure 2:
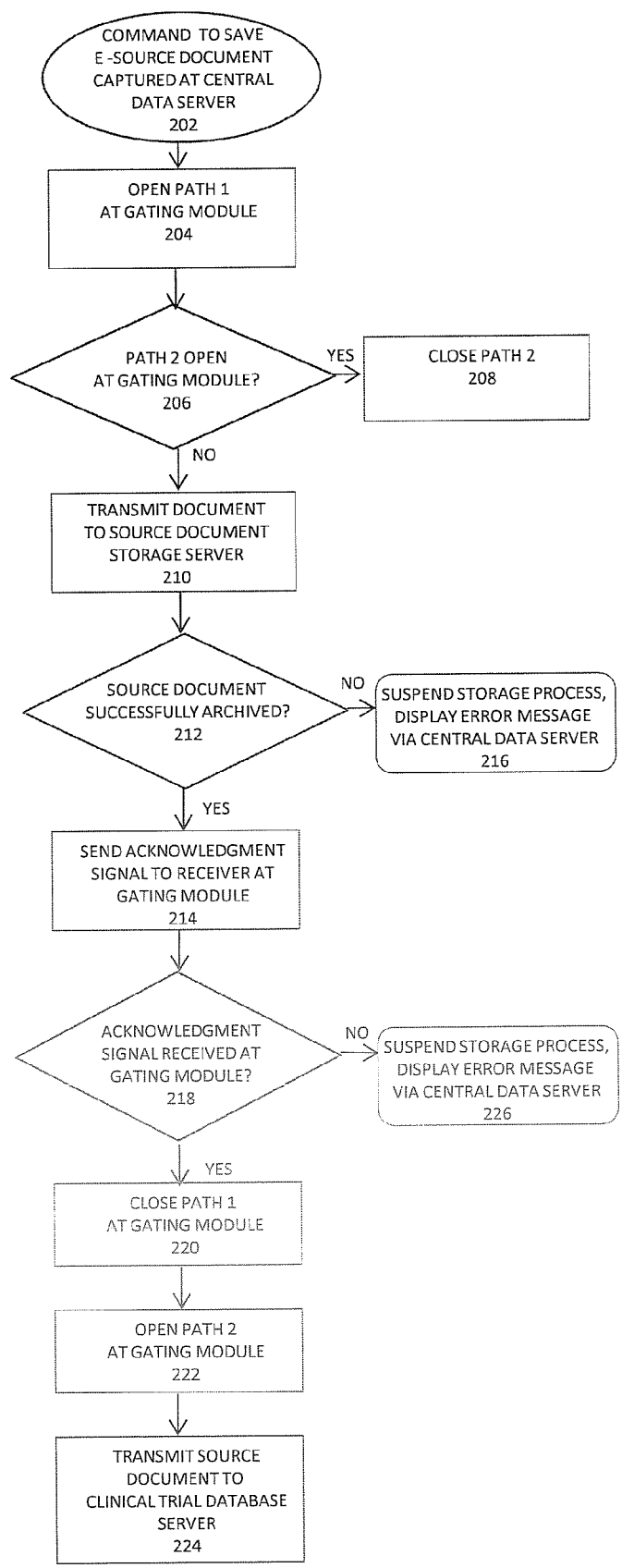
FIG. 2 represents a flow chart of an exemplary method for enforcing the archiving of electronic source documents in the present invention.

A flow chart depicting an exemplary method for enforcing the archiving of electronic source documents before admitting them to the clinical trial database server 18 is diagrammed in FIG. 2. An authorized user at a user interface commands the saving of an electronic source document which has been captured at the central data server, at 202. In response, the gating module 22 opens path 1 connecting the central data server 14 to the source document storage server 20, at 204. If path 2 connecting the central data server 14 to the clinical trial database server 18 is open, at 206, the gating module closes path 2, at 208. The electronic source document is transmitted to the source document storage server 20, at 210. If the document is successfully archived, at 212, an acknowledgment signal is sent from the acknowledgment signal transmitter 26 at the source document storage server 20 to the acknowledgment signal receiver 28 at the gating module 22, at 214. If the document has not been successfully archived, at 212, no acknowledgment signal is sent, and the storage process is suspended, at 216. Preferably, an error message is also sent to the user, at 216. If an acknowledgment signal is received by the gating module signal receiver 28, at 218, the gating module 22 opens path 2 connecting the central data server 14 to the clinical trial database server 18, at 220, and preferably closes path 1, at 222. The central data server 14 then transmits the source document to the clinical trial database server 18, at 224. If no acknowledgment signal is received by the gating module signal receiver 28, then the storage process is suspended, and an error message is preferably sent to the user, at 226.

The gating module 22 is preferably situated within the central data server 14, but it can also be situated within the source document server 20 or can be included in a discrete device operatively interconnecting the central data server 14 to the secure source document server 20 and the clinical trial database server 18. The gating module 22 can include a mechanical gating switch (not shown) of any type known in the art. Alternatively, the opening and closing of paths 1 and 2 can be controlled by logic circuits within a processor (not shown) situated in the gating module 22.

To facilitate the enforced archiving function of the gating module 22, the operating software of central database server 14 is preferably configured to bar a new or modified electronic source document from being transmitted by any route other than through the gating module 22. For example, an authorized user can retrieve an eCRF from the clinical trial database 18 and transmit it to the central data server 14 in order to add or modify data elements. When the user submits the modified eCRF for capture and storage, the central data server 14 recognizes the linked document attribute "source document" and responds by routing the eCRF to the gating module 22, to ensure archiving at the source document storage server 20 before transmission to the clinical trial database server 18.

In the preferred embodiment, the records management system 10 also includes a copy certification module 30 to perform the steps required to create an unmodifiable digital image copy of a paper source document, with the unmodifiable digital image copy being permanently attached to an electronic signature certifying that the digital image copy is an exact copy having all of the same attributes and information as the original paper document. This certified digital image copy meets FDA requirements for a certified copy of a source document, and can therefore be treated as an electronic source document.

Figure 3:
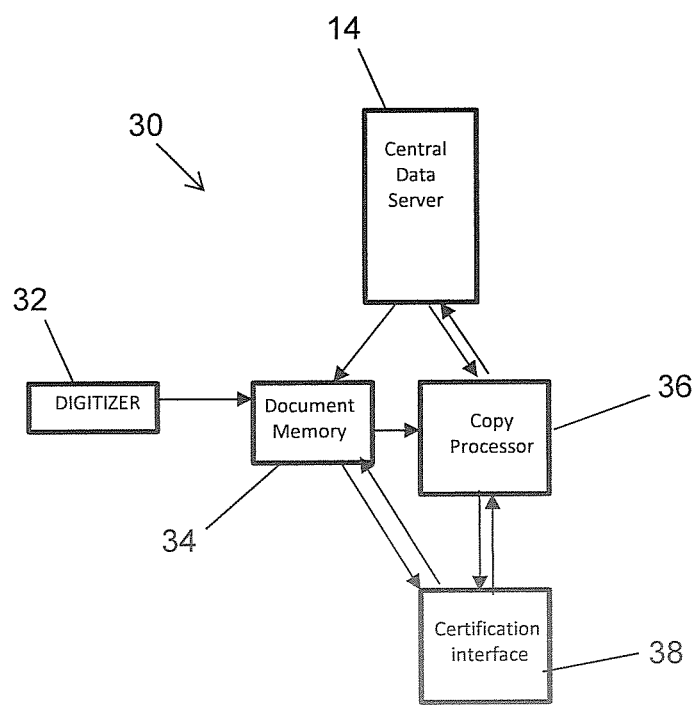
FIG. 3 represents a conceptual diagram of a certification module according to the present invention with solid arrowheads indicating the flow of information among components of the system.

The copy certification module 30, best shown in FIG. 3, includes a document digitizer 32 to generate a modifiable digital image copy of a paper source document; a document memory 34 operatively connected to the document digitizer 32, to store the digital image copy; a copy processor 36 operatively connected to the document memory 34 and the central data server 14, to attach an electronic signature to the modifiable digital image copy, to certify the modifiable digital image copy, and then render the certified digital image copy unmodifiable; and a certification interface 38 operatively connected to the document memory 34, to the copy processor 36, and to the central data server 14. The certification interface 38 displays the digital image copy of a source document for comparison with the original paper source document. The certification interface 38 also transmits user commands to the copy processor 36 to permanently attach a digital signature to certify digital image copy. The communicative connection between the copy processor 36 and the central data server 14 permits the transmission of the finished certified digital image copy to the central data server 14, from which it is routed to the gating module 22 for archiving in the source data storage server 20 and transmission to the clinical trial database server 18.

In the preferred embodiment, the certification interface also runs software operable to create and populate a human-readable certification form including a history of data-related events associated with a source document, insert a user's digital signature upon the user's command, and permanently incorporate the human readable certification form into a digital image copy before the copy is rendered unmodifiable.

The digitizer 32 can include a scanner or digital camera (not shown) or any digitization device known in the art to convert a paper document into a digital image for uplo32 is a separate device independent of the electronic records management system 10, and the uploading of a digital image into the document memory 34 is performed by any networking means known in the art, or by means of a transportable physical storage medium.

The document memory 34 includes at least one memory device of any suitable type, operatively connected to the digitizer 32 and the copy processor 36. The steps of digitizing a paper source document and creating a certified digital image copy need not be performed concurrently. The communicative connection between the document memory 34 and the central data server 14 permits a digital image copy to be stored in the central data server 14 and later retrieved into certification module 30 for the creation of a certified digital image copy.

A copy processor 36 according to the present invention includes any electronic processor with the capability of running any software known in the art to render a digital image copy unmodifiable. Preferably, the copy processor 36 runs software that can create and display an image in a modifiable format and then save it in a locked, "read only" format. For example, the processor can run Adobe Acrobat® software, paste a JPEG or TIF image of a source document into a PDF file, and then save the file as a locked, read-only PDF file.

In the preferred embodiment, the copy processor 36 also includes image editing software enabling a user to adjust, or command the automatic adjustment of, image quality properties of a digital image copy, before the copy is rendered unmodifiable. Image quality properties include such properties as image size, brightness, and contrast, and cropping. The image editing software is preferably incapable of editing or altering text, or performing operations that could alter the informational content of a digitized image, such as erasing, dodging, or airbrushing. The image editing software also preferably includes the capability of attaching a human-readable certification form to the digital image copy prior to rendering the digital image copy unmodifiable.

A certification interface 38 according to the present invention includes any computer or other processor configured to display a digital image copy of a document on a suitable monitor or other display. The certification interface 38 also includes a graphical user interface (GUI) (not shown) to enable a user to issue commands to the copy processor 36 to permanently affix the user's electronic signature to the digital image copy, render the digital image copy unmodifiable, and transmit the certified digital image copy to the central data server 14 for archiving at the source document storage server 20. The certification interface 38 is not necessarily a dedicated device, but can instead represent one aspect of an existing computer or other device such as, but not limited to, an originator's or investigator's desktop, laptop, or tablet computing device, or a smart phone or other hand held device.

In the preferred embodiment, the certification interface 38 also runs software for creating the human-readable certification form and for commanding the copy processor 36 to incorporate the form into the digital image copy. The certification interface 38 also populates the certification form with required information such as the unique identifiers of the original document and of the copy, the date and time of certification, and a signed statement that the signer has certified the electronic image copy as an exact copy having all of the same attributes and information as the original document. The certification interface 38 can additionally populate the certification form with any information required for the maintenance of an audit trail, including but not limited to the identity of the originator of data in the document, the date and time of origination and of copying, and the date and time of certification. The certification interface 38 can draw this information automatically from the central data server 14 or other storage device. Alternatively, the information can be entered manually via the GUI of the certification interface 38, or by a combination of automatic transfer and manual entry. The advantage of the human readable certification form is that it makes the audit trail and certification immediately visible to auditors when a digital image copy of a source document is displayed at a remote access interface.

Figure 4:
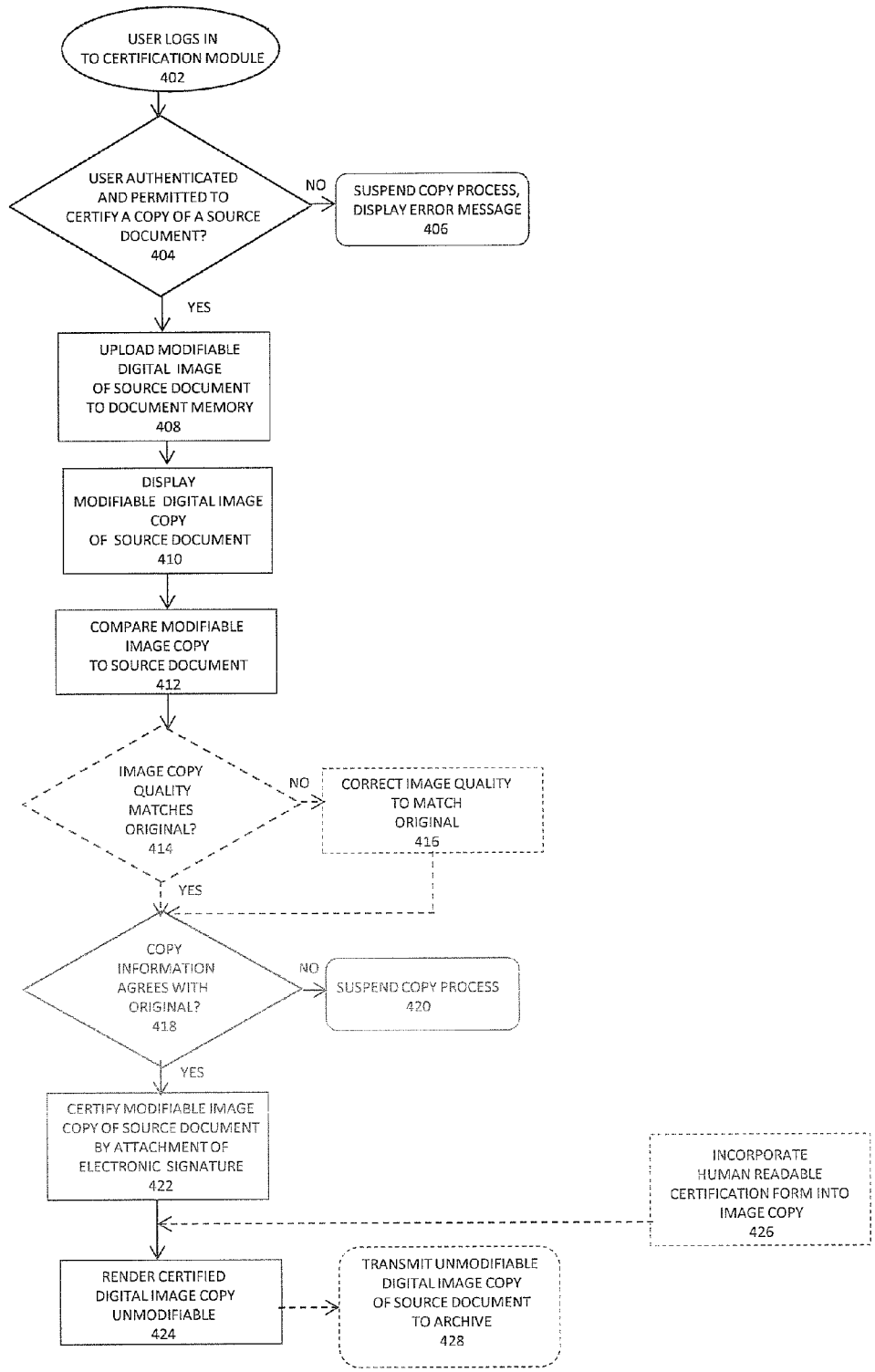
FIG. 4 represents a flow chart of an exemplary method for creating a certified electronic copy of a paper source document, with optional steps depicted with dotted outlines and arrows.

A flow chart depicting an exemplary method of operation of the certification module 30 is diagrammed in FIG. 4. A user initiates the certified copying process by logging into the certification interface 38 at 402. The log-in process includes the submission of electronic credentials showing the user to be an authorized user of the system, and to have permission to create and certify digital image copies of paper documents. If the user's authentication and/or permission is found to be deficient, at 404, the certification interface 38 displays an error message on the GUI and aborts the certification process, at 406. If the user's authentication and authority are sufficient, at 404, the user uploads a modifiable digital image copy of the original document into the document memory 34 of the copy certification module 30, at 408. The copy processor 36 accesses the modifiable digital image copy and displays it on the GUI of the certification interface 38, at 410. The user compares the modifiable digital image copy to the paper source document, at 412. The user makes comparisons with respect to both informational content and, optionally, of image quality.

If the user determines the image quality of the digital image copy to be discrepant from that of the original document, at 414, the user next uses the image editing software of the copy processor 36 to adjust the image until its image quality matches that of the original paper document, at 416. If the user determines that the informational content of the digital image copy is discrepant from that of the original document, to the point that the user cannot attest that it is an exact copy of the original, at 418, then the user aborts the copy certification process, at 420. If the user can attest that the digital image copy is an exact copy of the original document, at 418, the user next commands the certification interface 38 to permanently attach a digital signature certifying that the electronic image copy is an exact copy of the original source document, at 422. The user then commands the copy processor 36, to render the digital image copy unmodifiable, at 424, as previously described.

In the preferred embodiment, a user also has the option of incorporating a human-readable electronic certification form into the digital image copy before the copy is rendered unmodifiable, at 426. Preferably, the certification form is incorporated by superimposing it onto the digital image copy, for example by commanding the copy processor 36 to paste the form onto a blank portion of the copied digital image by means of the image editing software. The digital image copy can include a blank frame to receive the certification form. Alternatively, the digital image copy and certification form can be included on separate pages of a single document, which is then rendered unmodifiable. For example, the digital image copy and certification form can be inserted by the copy processor 36 onto successive pages of a PDF or Microsoft Word document, with the document immediately saved in a permanently locked "read only" format.

Once a certified unmodifiable digital image copy of a source document has been created by the certification module 30, it is preferably transmitted to the to the previously described gating module 22, via the central data server 14, for archiving. The certified unmodifiable digital image copy of a paper source document is itself a source document under 22 CFR 11 as interpreted by ICH E6 Sec. 1.52, and so can be archived as an electronic clinical trial source document.

In the preferred embodiment, the electronic records management system 10 also includes an electronic health records database server 40 to maintain an electronic health records database 42 containing the electronic health records of the individual subjects in the clinical trial. The electronic health records database server 40 is communicatively connected to the clinical trial database server 18 to permit the export of clinical trial data to the electronic health records database to update the health records of individual clinical trial subjects. The electronic health records database server is optionally also communicatively connected to the source document storage server 20 to receive data extracted from electronic source documents. In the preferred embodiment, the individual health records are accessible (based on assigned permissions) to health-care providers at remote clinical sites, in the same manner as a paper medical chart. The present invention includes at least one provider interface 42 to enable authorized health care providers to access the electronic health records server 40. The integration of a clinical trial database with individual health records allows prompt and efficient updating of a patient's health record with information produced by the clinical trial. This is a novel way for individuals to benefit from participation in a clinical trial, and it will in turn facilitate the recruitment of individuals into clinical trials.

The clinical trial database server 18 of the present invention is preferably linkable to the database servers of different clinical trials being run by authorized participants. Authorized users can thereby link patient records between different clinical trials. For instance, if a patient is participating in more than one clinical trial, the record of that patient in a first clinical trial can be linked to the record of the same patient in a second clinical trial. This functionality presents an additional dimension to clinical research, which was not previously attainable.

All data and document transmissions occurring within the system of the present invention are encrypted to ensure the security of the data. Additionally, in the preferred embodiment, while data which are transmitted to the clinical study database will generally not include a patient's name or identity, the system 10 will assign and/or include other identifying factors such as clinical trial number, site number, and/or patient number. Preferably, these assignments are made by the central data server 14 under rules administered via the console 16. The system 10 of the present invention also incorporates the use of unique user accounts and passwords for each system user. A system administrator, via the console 30, assigns each system user a user ID and password, which are used when logging onto the system. Each user is assigned specific permissions by the administrator. The use of unique user ID"s is also critical to the operation of the present invention's audit trail functionality, as described below.

Throughout the operation of the system, all data-related events are logged and stored in an audit trail. The present invention maintains a comprehensive audit trail log and history of all data-related activity and communication occurring within the system, specifically events related to data capture, editing, and access. Preferably, the audit trail information is collected directly from the data element attributes of electronic source documents and eCRFs at the moment they are captured at the central data server 14. This ensures the integrity of the collected data, by keeping a comprehensive record of all data-related events. This audit trail functionality is particularly significant within the clinical trial database server 18, where the integrity of the collected data is of paramount importance. Any modification of data in an electronic source document retrieved from the clinical trial database server 18 requires the modifying party to add data element identifiers including the party's identity and the reason for the modification. As previously described, these data element identifiers are both linked to the electronic source document and stored in a log. preferably within the central data server 14.

While in the preferred embodiment the present invention is directed towards data collection, processing, and storage for electronic health records and clinical trials, the system and method of the present invention can be applied in a broad range of industries and settings. Any setting or industry requiring the maintenance of discrete data records which are derived from a single set of data or a single data collecting event can benefit from the increased efficiency and data integrity provided by the present invention. The electronic records management system 10 of the present invention is easily adapted to the mortgage industry and to legal practices in wills and trusts. These entities often utilize documents which must exist in both circulating and original versions, and so will benefit from the forced archiving feature of the present invention, which prevents accidental modification of original electronic documents. The capacity of the present invention to create certified digital image copies of paper documents can reduce or eliminate the burden of maintaining and inventorying stored paper legal documents.

The invention has been described in an illustrative manner, and it is to be understood that the terminology used is intended to be in the nature of words of description rather than limitation.

Obviously, many modifications and variations of the present invention are possible in light of the above teachings. It is, therefore, to be understood that within the scope of the appended claims, the invention may be practiced otherwise than as specifically described.

The invention claimed is:
1. An electronic records management system for ensuring that an electronic clinical trial source document is archived under the control of a disinterested party before being released to a clinical trial database, consisting of:
   a central data server in communication with a copy certification module, the copy certification module configured to generate a digital image copy of a paper clinical trial source document, certify the digital image copy of the paper clinical trial source document as an exact unmodifiable copy of the paper clinical source document, and transmit the certified digital image copy to the central data server as an electronic source document;
   a central data server in communication with at least one data origination device, configured to capture clinical trial data from the at least one data origination device as an electronic source document, and configured to control the flow of said electronic source document through said records management system;
   a clinical trial database in communication with said central data server, configured to store an electronic source document for access by authorized participants in a clinical trial;
   a source document storage server in communication with said central data server, configured to archive said electronic source document, said source document storage server being under the control of a party disinterested in said clinical trial, said source document storage server including an acknowledgment signal transmitter configured to transmit an acknowledgment signal upon the archiving of said electronic source document, and a message mechanism configured to send an error message to a user when no acknowledgement signal is sent; and
   a gating module configured to ensure that said electronic source document is transmitted to said clinical trial database server only after said electronic source document has been successfully archived in said source document storage server without deleting said electronic source document from said source document storage server at any time, said gating module further configured to define a first path communicatively connecting said central data server with said source document storage server, and to allow transmission of said source document from said central data server through said gating module to said source data document server;
   said gating module further configured to define a second path communicatively connecting said central data server with said clinical trial data server, and to allow transmission of said source document from said central data server through said gating module to said clinical trial database server, said gating module further including an acknowledgment signal receiver configured to receive said acknowledgment signal transmitted by said source document storage server after said electronic source document has been successfully archived, said gating module further configured to open said second path and to close said first path only upon receipt of said acknowledgment signal such that said first path and second path are never simultaneously open.

2. A method for the collection, capture, processing, storage and tracking of data for both electronic clinical trial and personal health records, consisting of the steps of:

generating a digital image copy of a paper clinical trial source document;

certifying the digital image copy of the paper clinical trial source document as an exact unmodifiable copy of the paper clinical source document;

transmitting the certified digital image copy to the central data server as an electronic source document;

collecting clinical trial data with an electronic medical device;

capturing the clinical trial data at a central data server as an electronic source document;

setting a gating module to transmit an electronic source document from the central data server through the gating module to a source document storage server in a first path;

archiving the electronic source document at the source document storage server without deleting the electronic source document from the source document storage server at any time and sending an acknowledgement signal from the source document storage server to a gating module acknowledgement signal receiver on the gating module;

sending a user an error message when the electronic source document has not been successfully archived in said archiving step;

setting the gating module to transmit the electronic source document from the central data server through the gating module to a clinical trial server in a second path only after the electronic source document has been successfully archived at the source document storage server and closing the first path such that the first path and second path are never simultaneously open;

storing the electronic source document at the clinical trial server; and exporting the clinical trial data from the electronic source documents at the clinical trial database to an electronic health records database to update the personal health records of individual clinical trial subjects.

\* \* \* \* \*